United States Patent
Vinik et al.

(10) Patent No.: US 7,166,439 B2
(45) Date of Patent: Jan. 23, 2007

(54) ASSAY FOR ANTI-INGAP ANTIBODIES

(75) Inventors: Aaron I. Vinik, Norfolk, VA (US); David A. Taylor-Fishwick, Norfolk, VA (US)

(73) Assignee: GMP Endotherapeutics, Inc., Fort Lauderdale, FL (US)

(*) Notice: Subject to any disclaimer, the term of this patent is extended or adjusted under 35 U.S.C. 154(b) by 131 days.

(21) Appl. No.: 10/376,046

(22) Filed: Feb. 27, 2003

(65) Prior Publication Data

US 2003/0166031 A1 Sep. 4, 2003

Related U.S. Application Data

(60) Provisional application No. 60/361,040, filed on Mar. 1, 2002.

(51) Int. Cl.
*G01N 33/53* (2006.01)
(52) U.S. Cl. ............ 435/7.92; 435/7.1; 435/7.93; 435/7.94; 436/518
(58) Field of Classification Search ............... 435/7.1, 435/7.92–7.94; 436/501, 518, 524, 164, 436/819
See application file for complete search history.

(56) References Cited

U.S. PATENT DOCUMENTS 5,840,531 A 11/1998 Vinik et al.
2002/0127624 A1* 9/2002 Vinik et al. ............... 435/7.92

FOREIGN PATENT DOCUMENTS

WO WO 96/26215 * 8/1996
WO WO 98/189313 * 5/1998

OTHER PUBLICATIONS

Voller Alister, Diagnostic Horizons, Dynasciences Corportion, Published by Microbiological Associates, vol. 2, No. 1, Feb. 1978, pp. 1-7.*
Wild, David, The Immunoassay Handbook, Chapter 2, pp. 49-77, 1994.*
Maggio, Edward, Enzyme-Immunoassay, CRC Press, 1979, pp. 188-190.*
Stevens, Christine, Clinical Immunology and Serology, A Laboratory Perspective, Chapter 10, Labeled Immunoassays, pp. 144-146, 1996.*
Rafaeloff, R. et al., "Cloning and Sequencing of the Pancreatic Islet Neogenesis Associated Protein (INGAP) Gene and Its Expression in Islet Neogenesis in Hamsters," *J. Clin. Invest.*, 1997, vol. 99, No. 9, pp. 2100-2109.
Zotto, H. et al., "Possible relationship between changes in islet neogenesis and islet neogenesis-associated protein-positive cell mass induced by sucrose administration to normal hamsters", *J. of Endocrinology*, 2000, vol. 165, pp. 725-733.

* cited by examiner

*Primary Examiner*—Long V. Le
*Assistant Examiner*—Gary W. Counts
(74) *Attorney, Agent, or Firm*—Lott & Friedland, P.A.; Michael J. Keller, Esq.

(57) ABSTRACT

A solid phase assay is used for detecting antibodies to $INGAP^{104-118}$ peptide, a 15-amino acid peptide that is the biologically active portion of islet neogenesis associated protein (INGAP). The isotype of the antibodies to $INGAP^{104-118}$ peptide can be determined. A kit can also be used in the detection of anti-$INGAP^{104-118}$ antibodies. Endogenous autoantibodies or antibody production during therapeutic treatment of a mammal with $INGAP^{104-118}$ can be monitored.

9 Claims, 6 Drawing Sheets

ANTI-INGAP ANTIBODY ASSAY

Anti-INGAP Antibody Assay System Sample Plate Layout

SEQUENCE LISTING

<160> NUMBER OF SEQ ID NOS: 4

<210> SEQ ID NO 1
<211> LENGTH: 15
<212> TYPE: PRT
<213> ORGANISM: hamster sp.

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 175
<212> TYPE: PRT
<213> ORGANISM: Hamster sp.

<400> SEQUENCE: 2

Met Met Leu Pro Met Thr Leu Cys Arg Met Ser Trp Met Leu Leu Ser
1               5                   10                  15

Cys Leu Met Phe Leu Ser Trp Val Glu Gly Glu Ser Gln Lys Lys
            20                  25                  30

Leu Pro Ser Ser Arg Ile Thr Cys Pro Gln Gly Ser Val Ala Tyr Gly
            35                  40                  45

Ser Tyr Cys Tyr Ser Leu Ile Leu Ile Pro Gln Thr Trp Ser Asn Ala
    50                  55                  60

Glu Leu Ser Cys Gln Met His Phe Ser Gly His Leu Ala Phe Leu Leu
65                  70                  75                  80

Ser Thr Gly Glu Ile Thr Phe Val Ser Ser Leu Val Lys Asn Ser Leu
                85                  90                  95

Thr Ala Tyr Gln Tyr Ile Trp Ile Gly Leu His Asp Pro Ser His Gly
                100                 105                 110

Thr Leu Pro Asn Gly Ser Gly Trp Lys Trp Ser Ser Ser Asn Val Leu
            115                 120                 125

Thr Phe Tyr Asn Trp Glu Arg Asn Pro Ser Ile Ala Ala Asp Arg Gly
            130                 135                 140

Tyr Cys Ala Val Leu Ser Gln Lys Ser Gly Phe Gln Lys Trp Arg Asp
145                 150                 155                 160

Phe Asn Cys Glu Asn Glu Leu Pro Tyr Ile Cys Lys Phe Lys Val
                165                 170                 175

<210> SEQ ID NO 3
<211> LENGTH: 14
<212> TYPE: PRT
<213> ORGANISM: hamster sp.

<400> SEQUENCE: 3

Gln Lys Ser Gly Phe Gln Lys Trp Arg Asp Phe Asn Cys Glu
1               5                   10

<210> SEQ ID NO 4
<211> LENGTH: 14
<212> TYPE: PRT
<213> ORGANISM: hamster sp.

<400> SEQUENCE: 4

Ile Ala Ala Asp Arg Gly Tyr Cys Ala Val Leu Ser Gln Lys
1               5                   10

ASSAY FOR ANTI-INGAP ANTIBODIES

CROSS REFERENCE TO RELATED APPLICATIONS

This application claims priority to U.S. Provisional Application Ser. No. 60/361,040 filed Mar. 1, 2002, which is herein incorporated by reference in its entirety.

FIELD OF THE INVENTION

The invention relates to the field of assays for antibodies. Specifically, the invention relates to antibodies raised in mammals against administered therapeutic agents.

BACKGROUND OF THE INVENTION

Pancreatic islets of Langerhans are the only organ of insulin production in the body. However, they have a limited capacity for regeneration. This limited regeneration capacity predisposes mammals to develop diabetes mellitus. Islet neogenesis associated protein (INGAP, SEQ ID NO: 2) plays a role in stimulation of islet neogenesis, in particular, in beta cell regeneration from ductal cells. $INGAP^{104-118}$ peptide (IGLHDPSHGTLPNGS, SEQ ID NO: 1), a 15-amino acid peptide comprising amino acids 104–118 of the INGAP protein, is biologically active and is capable of inducing islet cell regeneration in an animal model. Pharmaceutical compositions containing a mammalian $INGAP^{104-118}$ peptide can be used for treatment of endocrine pancreatic insufficiency which may result from diabetes mellitus.

Antibodies to $INGAP^{104-118}$ peptide may be generated in patients following repeated dosing of $INGAP^{104-118}$ peptide or may be generated as autoantibodies to the endogenous protein, which may mitigate the action of INGAP or serve as a diagnostic marker for diabetes. Thus, there is a need in the art for a convenient assay for detecting antibodies that may be raised in a subject following treatment with $INGAP^{104-118}$ peptide.

BRIEF SUMMARY OF THE INVENTION

One embodiment of the invention is a method for detecting antibodies to $INGAP^{104-118}$ peptide in a test sample. This method comprises contacting a test sample which comprises serum of a mammal with $INGAP^{104-118}$ peptide bound to a solid support. The contacting is done under conditions sufficient for binding an anti-$INGAP^{104-118}$ antibody to the $INGAP^{104-118}$ peptide. The solid support is contacted with a detection antibody which specifically binds antibody molecules of all isotypes of the mammal. The detection antibody bound to the solid support is determined. Detection antibody bound to the solid support indicates that the test sample contains antibodies to $INGAP^{104-118}$ peptide.

A second embodiment of the invention is a method for detecting antibodies to $INGAP^{104-118}$ peptide in a test sample and determining the isotype of said antibodies. This method comprises contacting a test sample which comprises serum of a mammal with $INGAP^{104-118}$ bound to a solid support. The contacting is done under conditions sufficient for binding an anti-$INGAP^{104-118}$ antibody to the $INGAP^{104-118}$ peptide. The solid support is contacted with an isotype-specific antibody which specifically binds antibody molecules of one isotype of the mammal. The isotype specific antibody bound to the solid support is determined. Detection antibody bound to the solid support indicates that the test sample contains antibodies to $INGAP^{104-118}$ peptide and that the antibodies to the $INGAP^{104-118}$ peptide are of the one isotype.

A further embodiment of the invention is a kit for detecting an anti-$INGAP^{104-118}$ antibody in the serum of a mammal. The kit comprises an $INGAP^{104-118}$ peptide and a detection antibody.

These and other embodiments of the invention provide the art with tools and methods for detecting antibodies that bind to $INGAP^{104-118}$ peptide which are useful for monitoring subjects during treatment with $INGAP^{104-118}$ peptide and identifying subjects with INGAP autoantibodies.

DETAILED DESCRIPTION OF THE INVENTION

Figure 1:
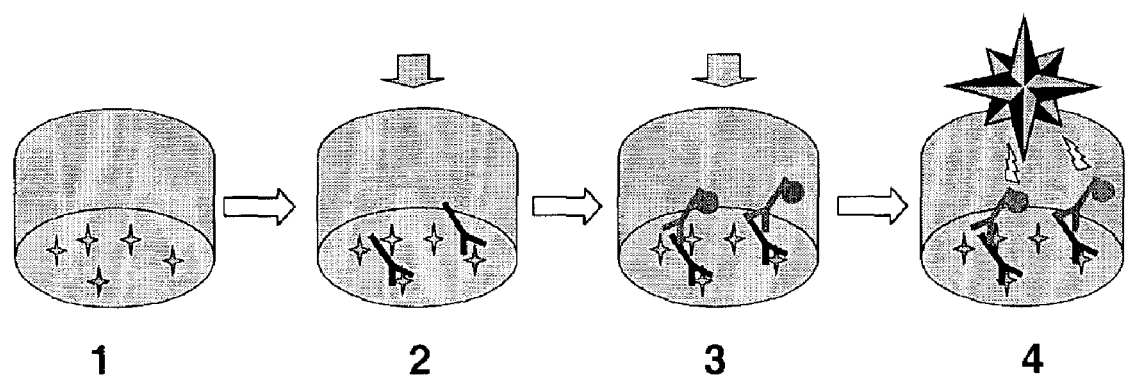
FIG. 1. Exemplary schematic of anti-$INGAP^{104-118}$ direct detection assay. Following the irreversible coating of peptide to the base of microtiter wells (1) test sample is added to wells (2). If antibodies specific for the peptide are present in the test sample they bind to the peptide and are retained in the wells after washing steps. The antibodies in contact with the peptide are detected by tagged-secondary antibodies which are subsequently added to the wells (3). Washing steps remove tagged-antibodies which are not in contact with the antibody-peptide complex. The presence of peptide-bound antibody is determined by reading the tag-signal in the wells (4).

It is a discovery of the present invention that anti-INGAP antibodies generated in vivo can be sensitively and specifically detected in a solid phase assay. Anti-INGAP$^{104-118}$ antibodies can be detected without interference by the components of mammalian serum. Normal human serum does not contain factors that result in false positive signals, nor does it inhibit the interaction of anti-INGAP$^{104-118}$ antibodies with INGAP$^{104-118}$ peptide.

Assays of anti-INGAP$^{104-118}$ antibodies in a sample from a mammal are useful to monitor generation of neutralizing antibodies during the therapeutic administration of INGAP$^{104-118}$ peptide. Neutralizing antibodies may be endogenous autoantibodies or antibodies generated in subjects following single or repeated dosing with INGAP$^{104-118}$ peptide. Anti-INGAP$^{104-118}$ antibodies can be specifically detected with sensitivity.

In a solid phase assay, purified INGAP$^{104-118}$ peptide can be immobilized on a solid support. Solid phase immunoassays are convenient for ease of separating bound from unbound components. Sequential immunoassay steps, including rinsing between steps and the binding of the detection antibody and development of the indicator reaction, can be easily performed without the need for expensive automation and skill.

Any test sample can be used, including but not limited to blood, plasma, or serum. The invention particularly contemplates test samples containing serum. Serum can be obtained from any mammal including, for example, mouse, rat, rabbit, guinea pig, monkey, dog, cat, cow, goat, pig, and human.

Test samples can be assayed at a single concentration of serum or at multiple concentrations which may be obtained by serial dilution of the serum. Diluent serum can be derived from the same species that is the source of the test sample. Other diluents such as buffers and normal saline can also be used. The highest serial dilution at which a signal can be detected can also be used to characterize a test sample. For example, the highest serial dilution at which a signal can be detected for a first mammal can be compared to that of a second mammal to obtain a relative measure of antibody titer in the first and second mammals.

Any immunoreactive form of INGAP$^{104-118}$, INGAP or a derivative thereof can be used. Native, synthetic, or recombinant forms of the whole INGAP peptide, or related proteins which contain, or are modified to contain the INGAP$^{104-118}$ sequence or portions immunoreactive with an antibody against INGAP$^{104-118}$ peptide may be used. Thus, portions of INGAP$^{104-118}$ peptide or peptides containing such portions and other residues or moieties can be used. Derivatives include, but are not limited to, modification the peptide's C-terminus, N-terminus, and/or amino acid side chains. Examples of C-terminal carboxylate modifications include esterification (e.g., benzyl, methyl or ethyl ester) and amidation. Examples of N-terminal modifications include acetylation and alkoxycarbonylation. Amino acid side chain modifications include methylation, benzylation, t-butylation, tosylation, alkoxycarbonylation, and the like.

INGAP$^{104-118}$ peptide, INGAP or a derivative thereof can be produced by any method known in the art. These methods include, but are not limited to inducing mammalian pancreatic cells to express INGAP protein by means of cellophane-wrapping (Rosenberg, L., Brown, R. A. and Duguid, W. P. (1982). Surg. Forum 33, 227–230). Standard recombinant techniques in prokaryotic or eukaryotic host cells can also be used to make full length or portions of INGAP or INGAP$^{104-118}$ peptide. Suitable host cells include bacteria, yeast, insect, or mammalian cells. Any expression vectors known in the art can be used. Enzymes can be used to generate less than full-length proteins by enzymatic proteolysis of full-length or partial proteins. Synthetic chemistry methods, such as solid-phase peptide synthesis, can be used to synthesize the proteins and polypeptides. The polypeptides can be synthesized directly on the solid support used for the immunoassay of the invention.

INGAP$^{104-118}$ peptide, INGAP protein, or portions thereof may be purified by means of any technique known in the art of protein purification. Exemplary techniques include ion-exchange chromatography, hydrophobic interaction chromatography, and immunoaffinity methods.

INGAP$^{104-118}$ peptide is bound to the solid support. It can be adsorbed or chemically coupled to a solid phase support. Any means known in the art for immobilizing a protein or peptide to a solid support can be used. INGAP$^{104-118}$ peptide can be either covalently or non-covalently bound to the solid phase support by techniques such as covalent bonding via an amide or ester linkage or adsorption. It can be bound using binding pairs such as biotin and avidin or antibody and antigen. After INGAP$^{104-118}$ peptide is affixed to the solid phase, the solid phase support can be incubated with a blocking solution (containing a blocking protein such as bovine serum albumin) to reduce non-specific adsorption of antibodies in a test sample to the support surface.

Various solid phase supports can be used, including but not limited to glass, polystyrene, polypropylene, nitrocellulose, dextran or other materials. Suitable forms of the solid phase supports include beads, microparticles, tubes, fabrics or plates formed from or coated with these materials. In a preferred embodiment the solid support comprises microtiter wells, such as a 96-well microtiter plate.

A detection antibody is used to assess anti-INGAP$^{104-118}$ antibody bound to the solid phase support. The detection antibody may be labeled. A label can be any composition which is detectable. Any analytical means known in the art can be used for determining or detecting the detection antibody. These means include the use of spectroscopy, chemistry, photochemistry, biocheimistry, immunochemistry, or optics. The label can be, for example, an enzyme (e.g., horseradish peroxidase, alkaline phosphatase, beta-galactosidase, and others commonly used in an ELISA), a radio-label (e.g., $^3$H, $^{125}$I, $^{35}$S, $^{14}$C, or $^{32}$p), a chemiluminescent compound (e.g. luciferin, and 2,3-dihydrophthalazinediones, luminol, etc.), a fluorescent dye (e.g., fluorescein isothiocyanate, Texas red, rhodamine, etc.), or any other dye known in the art.

The label may be coupled directly or indirectly (e.g., via binding pairs such as biotin and avidin) to the detection antibody according to methods well known in the art. As indicated above, a wide variety of labels may be used. The choice of label may depend on sensitivity required, ease of conjugation with the compound, stability requirements, available instrumentation, or disposal provisions. For a review of various labeling or signal producing systems which may be used, see U.S. Pat. No. 4,391,904.

Detection antibodies can be detected or determined by any suitable method known in the art. A label on an antibody can be detected by a gamma counter if the label is a radioactive gamma emitter, or by a fluorimeter, if the label is a fluorescent material. In the case of an enzyme, the label can be detected colorimetrically employing a substrate for the enzyme. In a preferred embodiment, the detection antibody is detected using alkaline phosphatase-conjugated, species-specific immunoglobulin. Any substrate of alkaline phosphatase can be used. For example, p-nitrophenylphosphate (pNPP) can be the substrate and the reaction product, p-nitrophenol, can be detected optically.

Results of the assay may be qualitative or quantitative. The amount of label associated with the support can be compared with positive and negative controls in order to determine the presence of anti-INGAP$^{104-118}$ antibodies. The controls are typically run concomitantly with the sample to be tested. A positive control can be a serum containing antibodies that are immunoreactive with the INGAP$^{104-118}$ peptide. A negative control can be a serum which does not contain antibodies that are immunoreactive with the INGAP$^{104-118}$ peptide. For quantitation, a standard curve using known quantities of anti-INGAP$^{104-118}$ antibody can be generated and/or used.

Antibodies for use as positive controls may be produced using all, or fragments of, the amino acid sequence of an INGAP protein. "Antibody" as used herein includes intact immunoglobulin molecules, as well as fragments thereof, such as Fab, F(ab')$_2$, and Fv, which are capable of binding an epitope of INGAP$^{104-118}$ peptide. Any type of antibody known in the art can be generated to bind specifically to an epitope of an INGAP$^{104-118}$ peptide. Monoclonal or polyclonal antibodies can be made as is well known in the art.

Any technique for purifying anti-INGAP$^{104-118}$ antibodies as are available in the art can be used. For example, antibodies can be purified by known methods such as affinity separation using protein A, high pressure liquid chromatography on reverse phase alkylated silica gel, or gel filtration. Antibodies can also be passed over a solid phase to which INGAP$^{104-118}$ peptide is bound. The anti-INGAP antibodies will bind to the INGAP$^{104-181}$ peptide bound to the solid support and the contaminants can be washed away. The bound antibodies can be eluted, for example, with a buffer having a high salt concentration.

The particular parameters employed in the assay of the present invention can vary widely depending on various factors such as the concentration of antibody in the sample, the nature of the sample, the type of immunoassay employed and the like. Optimal conditions can be readily established by those of ordinary skill in the art. Typical assay conditions include a temperature range of about 4° C. to about 45° C. and a pH value range of about 5 to 9. Incubation times can vary widely depending upon the nature of the assay, and generally range from about 0.1 minute to about 24 hours. A wide variety of buffers, for example TRIS-buffered saline, may be employed, and other reagents such as salt to enhance ionic strength, proteins such as serum albumin, stabilizers, and non-ionic detergents may also be included. Exemplary conditions are given in Example 2.

The isotype of an anti-INGAP$^{104-118}$ antibody, e.g., IgG, IgD, IgE, IgA, or IgM, can be determined. The biological functions and biochemical characteristics of isotypes differ and the isotype of antibodies present in a test sample can characterize the type of immune response in a subject. Thus, distinguishing the isotypes of immunoglobulin molecules present in a sample can be useful. Any method known in the art to determine antibody isotypes is contemplated. For example, isotype determination can be carried out on a solid support which is bound with INGAP$^{104-118}$ peptide. The sample to be tested can be contacted with the peptide-bound solid support and a detection antibody can be used. The detection antibody used for this purpose can be isotype-specific. The isotype-specific detection antibody can be labeled and detected as described above. Antibody subisotypes can also be determined by any method known in the art.

Another embodiment of the present invention is a kit for detecting anti-INGAP$^{104-118}$ antibodies in a mammalian serum. The kit can be useful, inter alia, for monitoring anti-INGAP$^{104-118}$ antibodies occurring spontaneously or produced during therapy which involves single or repeated dosing of an individual with INGAP$^{104-118}$. The kit will typically contain in a divided or undivded container an INGAP$^{104-118}$ peptide which can be used, inter alia, to coat a solid support. Alternatively, the kit can contain a solid support which is already coated with INGAP$^{104-118}$ peptide. The kit may also contain anti-INGAP$^{104-118}$ antibodies to serve as a positive control and for use in a standard curve. A detection antibody which is species specific, but isotype-generic can also be included. The detection antibody may be detectably labeled. The kit may also contain isotype-specific detection antibodies for determination of antibody isotype. Instructions, standard curves, and buffers can be optionally included in the kit.

The following examples are merely exemplary and are not intended to limit the scope of the invention.

EXAMPLE 1

Specificity of anti-INGAP$^{104-118}$ antibodies

Figure 2:
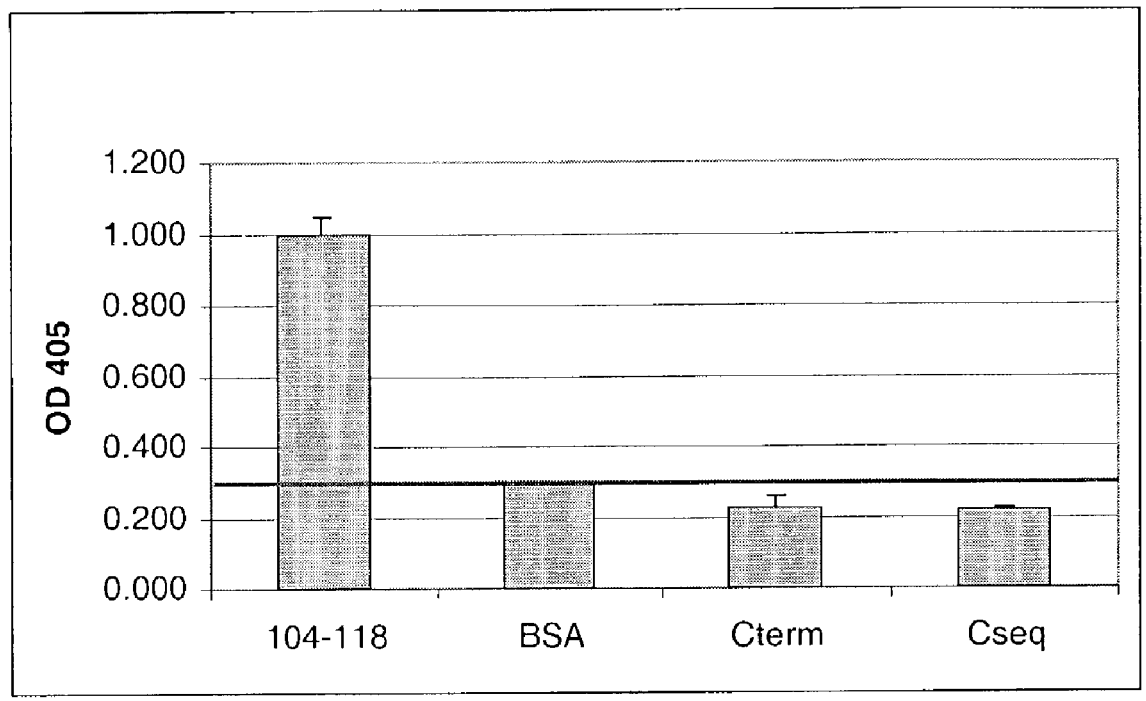
FIG. 2. Specificity of the rabbit antibody generated against $INGAP^{104-118}$ peptide. Rabbit anti-$INGAP^{104-118}$ peptide was incubated in microtiter wells pre-coated with either $INGAP^{104-118}$ peptide (SEQ ID NO: 1), bovine serum albumin (BSA), $INGAP^{151-164}$ (Cter SEQ ID NO: 3), or $INGAP^{139-152}$ (Cseq SEQ ID NO: 4). All wells were coated with an equivalent concentration of protein. Anti-$INGAP^{104-118}$ antibody was detected using alkaline phosphatase-conjugated, anti-rabbit IgG in combination with p-nitrophenylphosphate and optical detection of p-nitrophenol at 405 nm. The horizontal line indicates the limit of background signal for the assay.

To examine the specificity of the rabbit anti-INGAP$^{104-118}$ antibody, rabbit anti-INGAP$^{104-118}$ antibody was incubated in microtiter wells pre-coated with INGAP$^{104-118}$, bovine serum albumin (BSA), INGAP$^{155-164}$ (Cterm), or INGAP$^{139-152}$ (Cseq). All peptide-coated wells had an equivalent concentration of peptide. Anti-INGAP$^{104-118}$ antibody binding was assessed using an anti-rabbit IgG alkaline phosphatase (AP) conjugate detection antibody. Samples were incubated with pNPP and the optical density (OD) monitored at 405 nm. FIG. 2 demonstrates that rabbit anti-INGAP$^{104-118}$ antibody binds specifically to INGAP$^{104-118}$ since-only wells containing anti-INGAP$^{104-118}$ antibody exhibited a significant OD$_{405}$ upon incubation with pNPP. It was concluded that this antibody specifically binds to INGAP$^{104-118}$ peptide enabling its use in assay development.

Sensitivity of anti-INGAP$^{104-118}$ antibodies

Figure 3:
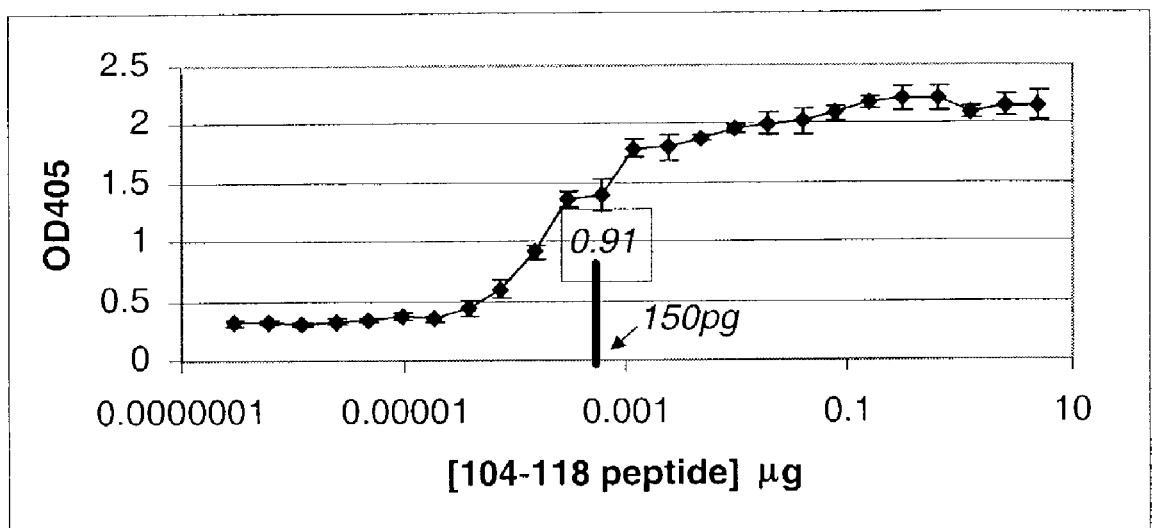
FIG. 3. Sensitivity of the rabbit antibody generated to $INGAP^{104-118}$ peptide. Rabbit anti-$INGAP^{104-118}$ antibody was incubated in microtiter wells pre-coated with various concentrations of $INGAP^{104-118}$ peptide. Detection of bound rabbit anti-$INGAP^{104-118}$ antibody was monitored using alkaline phosphatase-conjugated, anti-rabbit IgG in combination with p-nitrophenylphosphate and optical detection of p-nitrophenol at 405 nm. The $EC_{50}$ was 150 pg and the lowest detectable amount which was significantly different from zero was 18 pg.

The sensitivity of rabbit anti-INGAP$^{104-118}$ antibody was determined by incubating rabbit anti-INGAP$^{104-118}$ antibody with various concentrations of INGAP$^{104-118}$ peptide in microtiter wells pre-coated with various concentrations of INGAP$^{104-118}$ peptide. The data is shown in FIG. 3. The EC$_{50}$ for INGAP$^{104-118}$ peptide in this assay was determined to be 150 pg/well and the lowest amount that was significantly greater than zero was 18 pg/well.

Figure 4A:
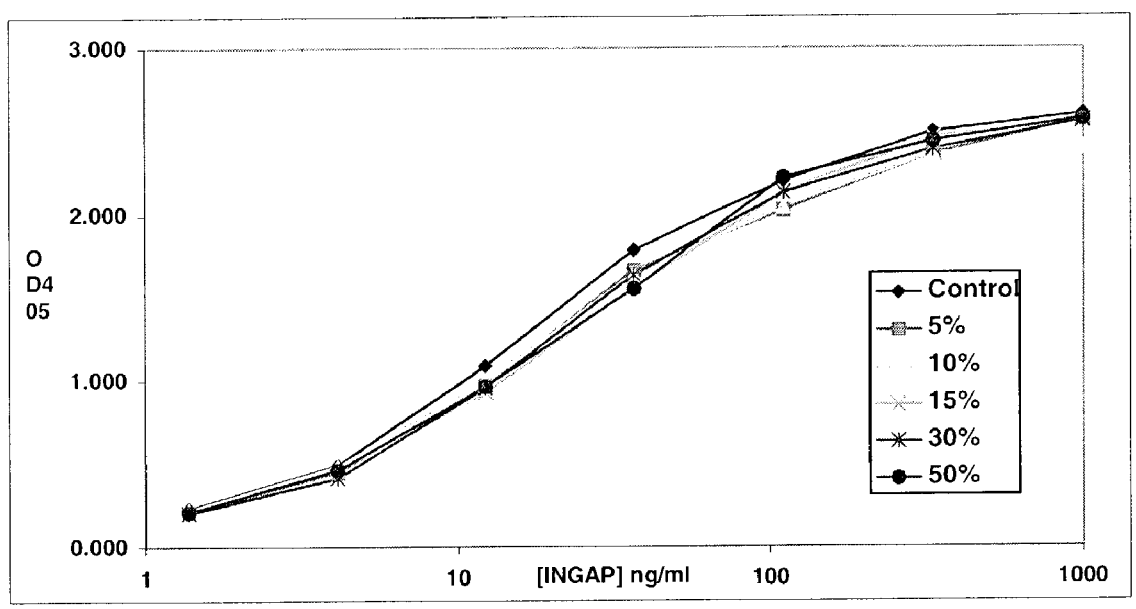
FIG. 4. Effect of human serum on detection of anti-$INGAP^{104-118}$ peptide antibody. (A) Each data point represents 2–1000 ng/mL anti-$INGAP^{104-118}$ antibody and 0 (◆), 5 (■), 10 (▲), 15 (×), 30 (*), or 50 (●) % normal human serum in microtiter wells. Detection of bound rabbit anti-$INGAP^{104-118}$ antibody was monitored using alkaline phosphatase-conjugated, anti-rabbit IgG in combination with p-nitrophenylphosphate and optical detection of p-nitrophenol at 405 nm. (B) Reaction was carried out as in (A), but no rabbit anti-$INGAP^{104-118}$ antibody was added. Data points correspond to 0 (◆), 5 (▲), 10 (*), 15 (+), 30 (−), and 50 % (●) normal human serum.

Normal human serum was found not to affect the anti-INGAP$^{104-118}$ antibody detection assay. To wells of a microtiter plate pre-coated with INGAP$^{104-118}$ peptide various concentrations of rabbit anti-INGAP$^{104-118}$ antibody were added. Anti-INGAP$^{104-118}$ antibody was serial diluted in buffer containing normal human serum at either 0% (control), 5%, 10%, 15%, 30% or 50%. See FIG. 4A. The binding of rabbit antibody was detected with anti-rabbit IgG conjugated to alkaline phosphatase (AP). No decrease in assay sensitivity was observed between 5 to 50% serum. However, the presence of human serum at concentrations greater than 50% can decrease the assay sensitivity up to 3-fold. From this data it was concluded that there are no factors present in normal human serum that significantly interfere with the interaction of anti-INGAP$^{104-118}$ antibody with INGAP$^{104-118}$ peptide.

Figure 4B:
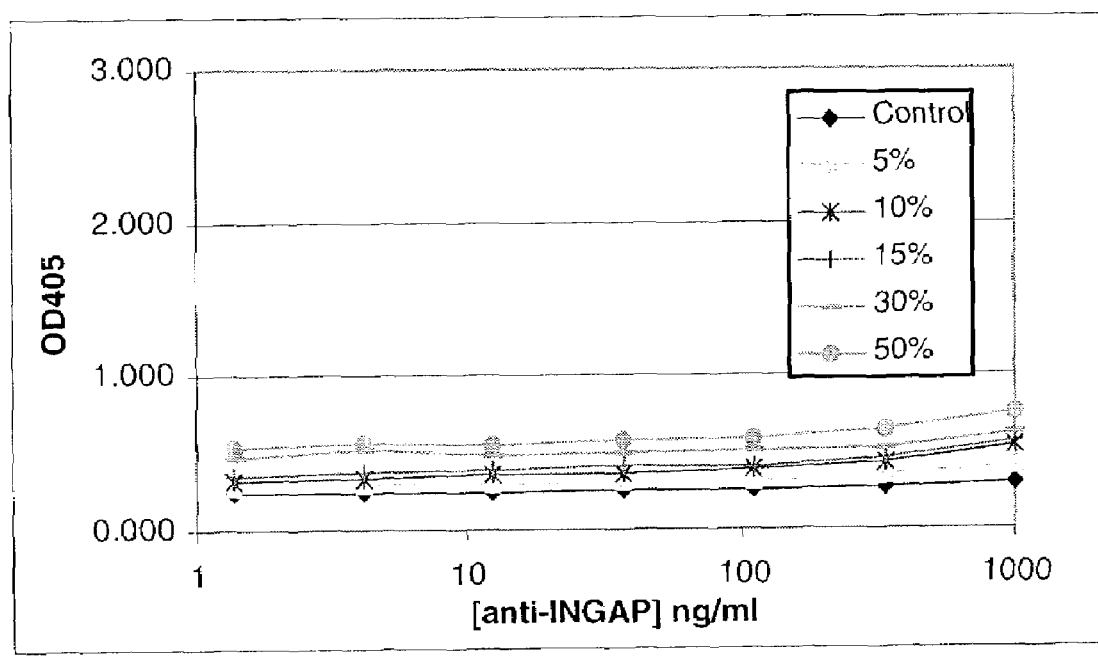
Figure 5:
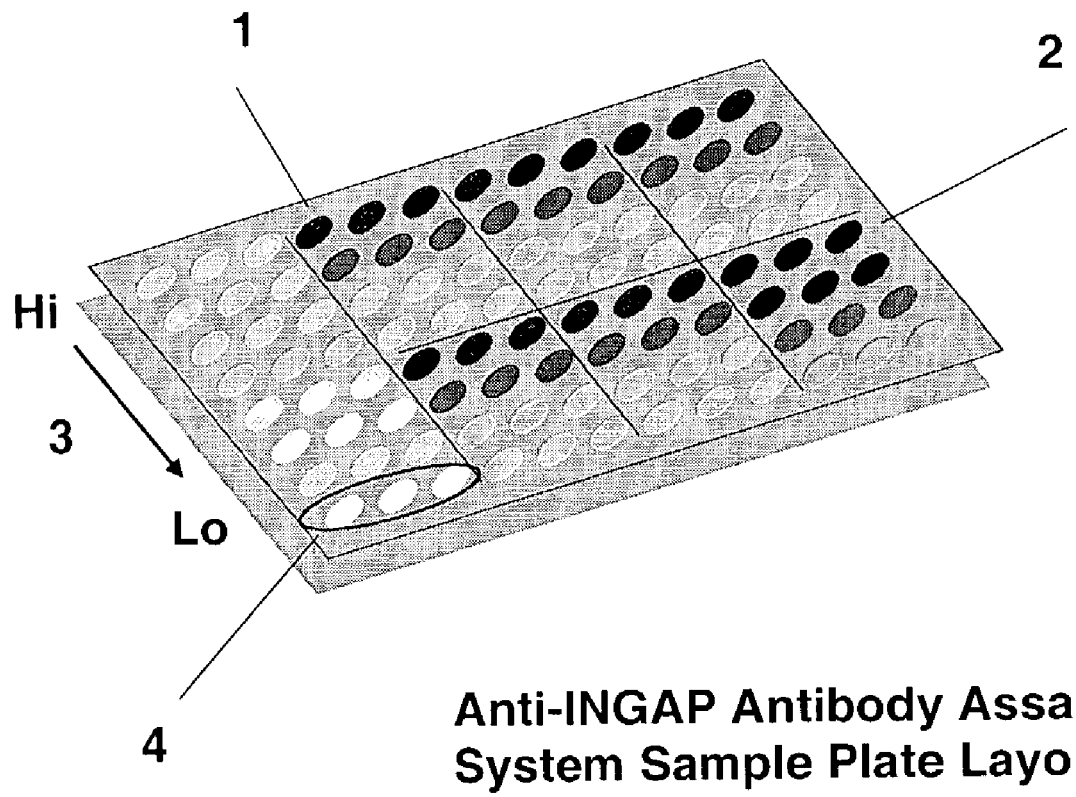
FIG. 5. Anti-$INGAP^{104-118}$ antibody assay sample plate layout. (1) Dilutions of patient serum samples. (2) Dilutions of standardized human sera. (3) Rabbit anti-$INGAP^{104-118}$ antibody standard curve. (4) Plate blanks prepared using highest concentration of rabbit anti-$INGAP^{104-118}$ antibody on wells not coated with $INGAP^{104-118}$ peptide.

It was also determined that there are no antibodies present in normal human serum that interact with INGAP$^{104-118}$ peptide. Following the same experimental protocol as described above, normal human serum was screened with AP-conjugated, anti-human immunoglobulin. No detection antibody was detected indicating that no antibodies present the normal human serum were capable of binding to INGAP$^{104-118}$ peptide. See FIG. 4B.

Based upon the data, the assay successfully detects INGAP$^{104-118}$ peptide specific antibodies. Moreover, the assay is functional in the presence of normal human serum. Therefore, this assay is suitable to screen for the presence of anti-INGAP$^{104-118}$ antibodies in patient sera. The assay is simple and can readily be streamlined to accommodate medium to high throughput screening of samples.

EXAMPLE 2

Immunoassay Protocol For anti-INGAP$^{104-118}$ In Human Serum

The reagents used in this example are as follows: TBS (0.05 M TRIS, 0.138 M NaCl, 0.0027 KCl, pH 8.0 at 25° C.), TBS-TW (TBS containing 0.05% Tween-20 (polyoxyethylene-borbitan monolaurate)), Blocking Solution for Matrix Dilution Buffer (TBS-TW containing 1% w/v bovine serum albumin), Secondary Antibody Detection for Human Sera (1:5000 dilution of anti-human IGg, AP conjugated (Sigma A-1543) in Blocking solution), Secondary Antibody Detection for Rabbit Antibody (1:5000 dilution of anti-rabbit IGg, AP conjugated (Sigma A-2556) in Blocking solution), Matrix Dilution Buffer (1:25 human serum:blocking solution, v/v), and pNPP Substrate Buffer (one set para-nitrophenyl phosphate tablets (Sigma N-1891) in 5 mL deionized water).

Rabbit anti-INGAP$^{104-118}$ antibody was supplied by Strelitz Diabetes Institute.

Standard Curve—Standard curve was prepared according to the following table:

| Calibration Standard | 250 ng/mL rabbit anti-INGAP$^{104-118}$ (μL) | Matrix Dilution buffer (μL) | Calibration Standard Concentration (ng/ml) | Matrix Concentration (ng/mL) |
|---|---|---|---|---|
| S-01 | 500 | — | 250 | 6250 |
| S-02 | 180 | 120 | 150 | 3750 |
| S-03 | 160 | 240 | 100 | 2500 |
| S-04 | 80 | 320 | 50.0 | 1250 |
| S-05 | 30 | 270 | 25.0 | 625 |
| S-06 | Using standard -03 30 | 270 | 10.0 | 250 |
| S-07 | Using standard -04 30 | 270 | 5.0 | 125 |

Assays were carried out in 96-well microtiter plates. Standards were prepared as indicated in the table shown above, making enough standard to add 100 μL in duplicate to each desired plate well. Desired standard concentrations were made by serial diluting rabbit anti-INGAP$^{104-118}$ antibody standard with Matrix Dilution Buffer.

A control serum sample was prepared from blank human serum in the same dilution range as the preparative samples. False positive results were not generated due to the concentration of the serum or any proteins in normal human serum that will cross react with the INGAP$^{104-118}$ peptide.

Plate blanks were prepared by adding 100 μL of the highest concentration standard to wells H1 and H2 on each subsequent plate. These wells were not coated with INGAP$^{104-118}$ peptide. All reagents should be added to these samples. Wells designated by the plate design served as the blank subtraction value for all wells used in that batch. When plate blanks were not available due to a second batch being analyzed on the same plate, the control blanks were used. FIG. 6 illustrates a representative sample assay plate layout.

All quality control samples were prepared in duplicate. All unknown samples were prepared in duplicate and 100 μL of each sample was diluted with 2400 μL Matrix Dilution Buffer before microtiter plate analysis.

Microtiter plate analysis was performed as follows: 100 μL of either standard, control blank, quality control sample or unknown sample was added to each plate well. The wells were covered with mylar covers and incubated at room temperature for at least 1 hour at room temperature or overnight at 4° C. The wells were washed by filling each well three times with TBS-TW, making sure to remove all excess liquid between washes. 100 μL of anti-human IgG AP-conjugated antibody was added to serum samples and control serum only. 100 μL of anti-rabbit IgG AP-conjugated antibody was added to calibration standards and quality control standards. These were incubated 1–2 hours at room temperature. Each well was washed once with TBS-TW and then twice with TBS, again making sure to remove all excess liquid between washes. To each well, 100 μL of pNPP substrate buffer was added. Color was allowed to develop for approximately 30 minutes or to the desired color intensity. The target value for the maximum color development was 2.5 OD for the highest calibration standard so the color development was monitored frequently. Multiple plate readings were obtained to monitor color development. Color development was read at ~30 minutes (development will vary with conditions). Overdevelopment occurs when the high standard is over the linear range of the instrument.

The standard curve was calculated using a point-point fitting based on the OD at 405 nm. All samples where the OD exceeds the highest point of the standard curve were re-prepared at an appropriate dilution. Sample results were calculated against the resulting point-to-point curve. Up to two non-consecutive points may be dropped from the curve based on obvious analytical errors or non-typical color development.

Quality control samples were considered acceptable if they were within 20% of theoretical.

Positive sera were defined as those samples with an OD$_{405}$ of greater than 0.800 at a dilution of 1:25. Sera comparison between positive patient samples were based on the titer (dilution of sera) required to give a standard signal readout (i.e. 0.800 OD$_{405}$ units).

What is claimed:

1. A method for detecting antibodies to a Islet Neogenesis Associate Protein peptide (INGAP$^{104-118}$) in a human test sample comprising: contacting the test sample with an Islet Neogenesis Associated Protein peptide of SEQ ID NO 1 bound to a solid support, wherein the contacting is under conditions sufficient for binding an anti-INGAP$^{104-118}$ antibody to the INGAP$^{104-118}$ peptide; contacting any bound test sample bound to the Islet Neogenesis Associated Protein peptide on the solid support with a detection antibody which specifically binds to antibody molecules of all antibody isotypes of the human; washing the solid support to remove any unbound antibody molecules to SEQ ID NO 1, and determining the detection antibody bound to the solid support, wherein detection antibody bound to the solid support indicates that the test sample contains antibodies to peptide of SEQ ID NO 1.

2. The method of claim 1 wherein amount of the detection antibody bound is compared to a standard curve generated using known amounts of an antibody to a peptide comprising SEQ ID NO 1; wherein the test sample is selected from the group consisting of blood, serum and plasma.

3. The method of claim 1 wherein multiple test samples are used which are serial dilutions of the test sample of the human wherein the serial dilutions show relative measure of titre in a test sample or between test samples from different sources.

4. The method of claim 3 further comprising: determining a highest serial dilution at which a signal is generated, said highest serial dilution being the test sample used to evaluate titer of anti-INGAP$^{104-118}$ peptide antibodies in the human.

5. The method of claim 4 wherein the highest serial dilution of a first human test sample is compared to a highest serial dilution of a second human test sample to provide a comparative measure of titer in the first and second human test samples.

6. The method of claim 1 wherein the detection antibody comprises a detectable label.

7. The method of claim 6 wherein the detectable label is an enzyme.

8. The method of claim 7 wherein the enzyme is selected from the group consisting of alkaline phosphatase, horseradish peroxidase and beta-galactosidase.

9. The method of claim 6 wherein the detectable label is selected from the group consisting of fluorescent molecules, chemiluminescent molecules, radioactive molecules, and dye molecules.

* * * * *